(12) United States Patent
Rich et al.

(10) Patent No.: US 7,588,733 B2
(45) Date of Patent: Sep. 15, 2009

(54) RETAINING CLIP FOR REAGENT TEST SLIDES

(75) Inventors: Carl Russell Rich, Falmouth, ME (US); Justin Jay Griffin, Scarborough, ME (US); Jonathan William Lawrence, Portland, ME (US); Ross Bryan Goldman, Scarborough, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 753 days.

(21) Appl. No.: 11/001,994

(22) Filed: Dec. 2, 2004

(65) Prior Publication Data
US 2005/0135971 A1 Jun. 23, 2005

Related U.S. Application Data

(60) Provisional application No. 60/526,885, filed on Dec. 4, 2003, provisional application No. 60/526,884, filed on Dec. 4, 2003.

(51) Int. Cl.
*B01L 3/00* (2006.01)
(52) U.S. Cl. .................. 422/102; 422/104; 422/99; 422/100; 422/58; 422/61
(58) Field of Classification Search ............. 422/57–58, 422/60–61, 99–100, 102, 104
See application file for complete search history.

(56) References Cited

U.S. PATENT DOCUMENTS

| 2,630,219 | A | 3/1953 | Pierce | |
|---|---|---|---|---|
| 2,919,021 | A | 12/1959 | Robinson et al. | ............ 353/118 |
| 2,942,365 | A | 6/1960 | Badalich | |
| 3,133,332 | A | 5/1964 | Johnson | |
| 3,244,273 | A | 4/1966 | Wiklund | |
| 3,416,250 | A | 12/1968 | Schweers | |
| 3,467,251 | A | 9/1969 | Janss et al. | |
| 3,552,846 | A | 1/1971 | Hansen | |
| 3,600,762 | A | 8/1971 | Rissberger, Jr. | ........... 24/81 FC |
| 3,624,873 | A | 12/1971 | Frey | |
| 3,701,558 | A | 10/1972 | Baker | |
| 3,710,975 | A | 1/1973 | Jansen | ......................... 220/31 |
| 3,711,905 | A | 1/1973 | Eckerdt et al. | ................ 24/263 |
| 3,756,393 | A | 9/1973 | Markwitz et al. | ............. 206/62 |
| 3,992,158 | A | 11/1976 | Przybylowicz et al. | ........ 23/253 |
| 4,053,381 | A | 10/1977 | Hamblen et al. | ............ 204/195 |
| 4,077,515 | A | 3/1978 | Shoberg | ..................... 206/456 |
| 4,081,119 | A | 3/1978 | Messmore | ................ 224/46 R |
| 4,114,166 | A | 9/1978 | Driscoll et al. | ................ 354/76 |
| 4,151,931 | A | 5/1979 | Scherer et al. | .............. 221/226 |

(Continued)

*Primary Examiner*—Brian R. Gordon
(74) *Attorney, Agent, or Firm*—Gerald T. Bodner

(57) ABSTRACT

A retaining clip for retaining reagent test slides in a stacked arrangement is formed as a unitary member and has first, second and third plates, each having an inner surface and an outer surface. The inner surface of the first plate pivots towards the inner surface of the second plate, and the inner surface of the third plate also pivots such that the inner surfaces of the first and third plates at least partially face each other upon pivoting. The inner surfaces of the first and third plates are separated by a distance to accommodate the reagent test slides in a stacked arrangement. Alternatively, the third and second plates can be fixed rigidly to each other with only the first plate pivoting to at least partially face the third plate upon pivoting.

36 Claims, 10 Drawing Sheets

U.S. PATENT DOCUMENTS

| | | | | |
|---|---|---|---|---|
| 4,159,875 A | 7/1979 | Hauser | ............... | 356/244 |
| 4,230,757 A | 10/1980 | Toner | ............... | 428/137 |
| 4,365,970 A * | 12/1982 | Lawrence et al. | ............... | 436/66 |
| 4,437,566 A | 3/1984 | Szahler | ............... | 206/1.5 |
| 4,440,301 A | 4/1984 | Intengan | ............... | 206/456 |
| 4,568,519 A | 2/1986 | Hamilton et al. | ............... | 422/64 |
| 4,584,275 A | 4/1986 | Okano et al. | ............... | 435/290 |
| 4,589,551 A | 5/1986 | Hellon | ............... | 206/456 |
| 4,635,791 A | 1/1987 | Jackson et al. | ............... | 206/210 |
| 4,645,743 A * | 2/1987 | Baker et al. | ............... | 436/66 |
| 4,689,858 A * | 9/1987 | Barber | ............... | 24/17 B |
| 4,696,396 A | 9/1987 | Samuels | ............... | 206/339 |
| 4,737,344 A | 4/1988 | Koizumi et al. | ............... | 422/100 |
| 4,766,714 A | 8/1988 | Sugaya | ............... | 53/242 |
| 4,776,689 A | 10/1988 | Maclay | ............... | 353/111 |
| 4,789,629 A * | 12/1988 | Baker et al. | ............... | 435/7.92 |
| 4,826,659 A | 5/1989 | Akisada | ............... | 422/63 |
| 4,828,111 A | 5/1989 | Rosenberg | ............... | 206/456 |
| 4,855,109 A * | 8/1989 | Muraishi et al. | ............... | 422/63 |
| 4,857,272 A | 8/1989 | Sugaya | ............... | 422/65 |
| 4,960,224 A | 10/1990 | Boenisch | ............... | 206/456 |
| 4,997,100 A * | 3/1991 | Dudek | ............... | 422/104 |
| 5,053,198 A | 10/1991 | Quenin | ............... | 422/64 |
| 5,080,869 A | 1/1992 | McCormick | ............... | 422/102 |
| 5,081,038 A | 1/1992 | Sugaya et al. | ............... | 436/46 |
| 5,089,229 A | 2/1992 | Heidt et al. | ............... | 422/64 |
| 5,090,568 A | 2/1992 | Tse | ............... | 206/456 |
| 5,102,624 A | 4/1992 | Muraishi | ............... | 422/64 |
| 5,119,573 A | 6/1992 | Dentella | ............... | 40/367 |
| 5,147,042 A | 9/1992 | Levy | ............... | 206/456 |
| 5,154,889 A | 10/1992 | Muraishi | ............... | 422/65 |
| 5,176,257 A | 1/1993 | Levy | ............... | 206/456 |
| 5,250,262 A | 10/1993 | Heidt et al. | ............... | 422/64 |
| 5,265,726 A | 11/1993 | Johnson | ............... | 206/456 |
| 5,292,000 A | 3/1994 | Levy | ............... | 206/456 |
| 5,297,383 A | 3/1994 | Mackay | ............... | 52/712 |
| 5,336,467 A | 8/1994 | Heidt et al. | ............... | 422/64 |
| 5,358,019 A | 10/1994 | Sumner, III | ............... | 150/147 |
| 5,358,692 A | 10/1994 | Reynolds | ............... | 422/104 |
| 5,436,129 A * | 7/1995 | Stapleton | ............... | 435/6 |
| 5,441,698 A * | 8/1995 | Norell | ............... | 422/58 |
| 5,507,388 A | 4/1996 | Kildal et al. | ............... | 206/459.5 |
| 5,538,688 A | 7/1996 | Tezuka et al. | ............... | 422/64 |
| 5,553,720 A | 9/1996 | Dardashti | ............... | 211/40 |
| 5,599,505 A | 2/1997 | Fujisaki et al. | ............... | 422/104 |
| 5,617,973 A | 4/1997 | Seto et al. | ............... | 221/56 |
| 5,653,942 A | 8/1997 | Terashima et al. | ............... | 422/63 |
| 5,674,454 A | 10/1997 | Karl et al. | ............... | 422/63 |
| 5,718,329 A | 2/1998 | Ippolito et al. | ............... | 206/38 |
| 5,877,028 A * | 3/1999 | Chandler et al. | ............... | 436/514 |
| 5,998,220 A | 12/1999 | Chandler | ............... | 436/514 |
| 6,006,911 A | 12/1999 | Levy | ............... | 206/456 |
| 6,017,767 A * | 1/2000 | Chandler | ............... | 436/514 |
| 6,033,627 A * | 3/2000 | Shields et al. | ............... | 422/58 |
| 6,395,234 B1* | 5/2002 | Hunnell et al. | ............... | 422/101 |
| 6,436,714 B1* | 8/2002 | Clawson et al. | ............... | 436/66 |
| 6,486,947 B2* | 11/2002 | Modlin et al. | ............... | 356/246 |
| 6,713,018 B2 | 3/2004 | Sugaya et al. | ............... | 422/58 |
| 6,773,676 B2* | 8/2004 | Schembri | ............... | 422/102 |
| 6,846,453 B1* | 1/2005 | Uesaka et al. | ............... | 422/58 |
| 6,890,729 B2* | 5/2005 | Mielzynska et al. | ............... | 435/40.5 |
| 7,001,776 B2* | 2/2006 | Botacini das Dores et al. | ............... | 436/518 |
| 7,273,591 B2* | 9/2007 | Sellers et al. | ............... | 422/104 |
| 2002/0039796 A1* | 4/2002 | Dores et al. | ............... | 436/177 |
| 2003/0186447 A1 | 10/2003 | Seto et al. | ............... | 436/48 |
| 2004/0071605 A1* | 4/2004 | Coonan et al. | ............... | 422/102 |
| 2004/0223890 A1* | 11/2004 | Summers et al. | ............... | 422/104 |
| 2005/0123444 A1 | 6/2005 | Tomasso et al. | ............... | 422/64 |
| 2005/0238541 A1* | 10/2005 | Barski et al. | ............... | 422/99 |

* cited by examiner

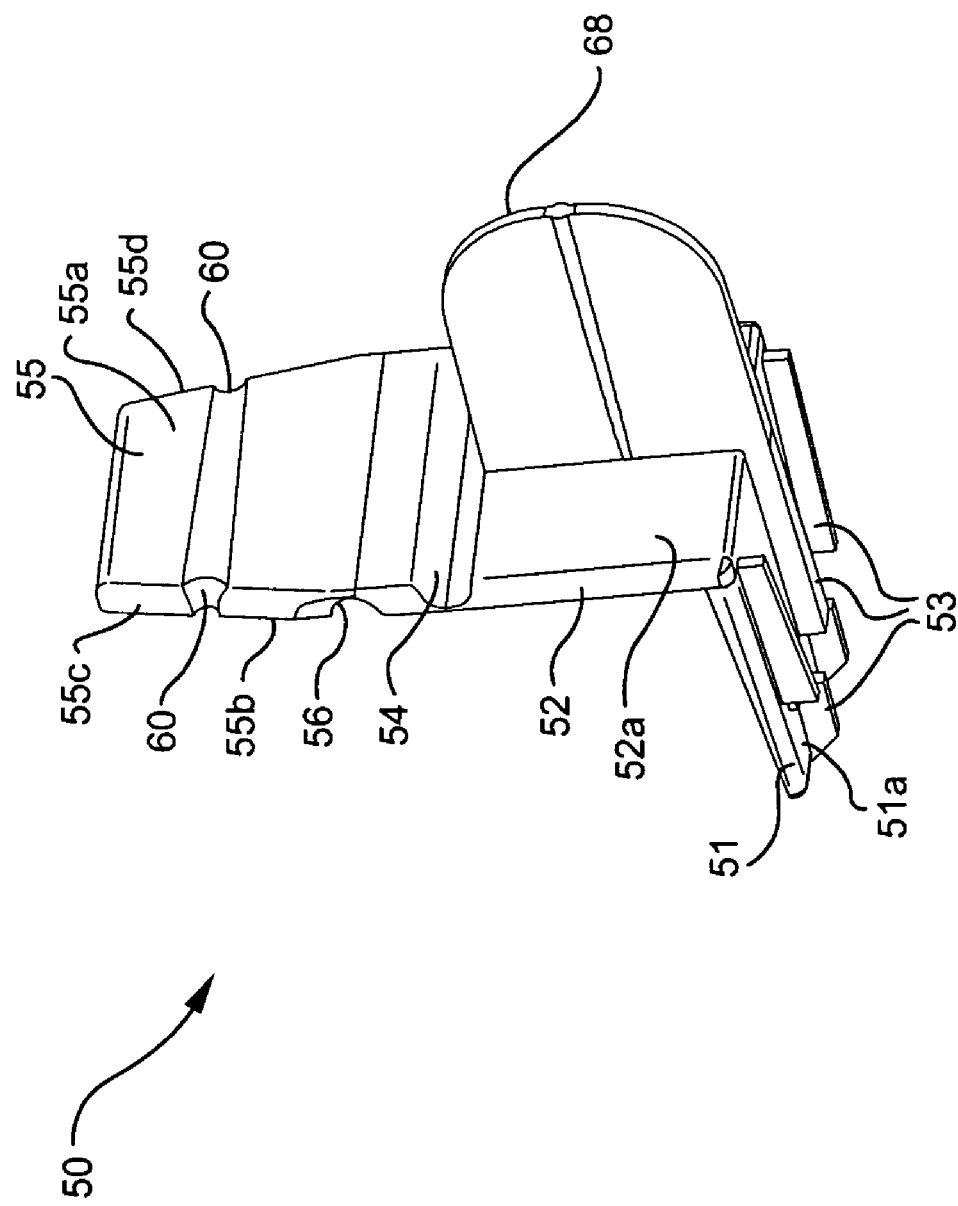

RETAINING CLIP FOR REAGENT TEST SLIDES

CROSS-REFERENCE TO RELATED APPLICATIONS

This application is related to U.S. provisional patent application Ser. No. 60/526,885, filed on Dec. 4, 2003, and entitled "Retaining Clip For Reagent Test Slides", and to U.S. provisional patent application Ser. No. 60/526,884, filed on Dec. 4, 2003, and entitled "Reagent Test Slide Injector Mechanism Having a Scotch Drive and Rotatable Turntable Having a Geneva Drive for a Chemical Analyzer", the disclosure of each of which is incorporated herein by reference. This application claims the benefit of priority under 35 U.S.C. 119 to the aforementioned related provisional applications.

BACKGROUND OF THE INVENTION

1. Field of the Invention

The present invention relates to chemical analyzers using dry chemistry reagent test slides, and more particularly relates to holding and storage devices for such reagent test slides prior to use and upon insertion of the test slides in a chemical analyzer.

2. Description of the Prior Art

Automated systems for carrying out quantitative chemical analysis of fluid samples have increasingly been developed for use with essentially dry, analytical elements which are preferably in the form of test slides. The test slides are formed as a multi-layer element containing the necessary reagents for reaction with components of a biological fluid, such as blood serum, deposited thereon. Certain reactions calorimetrically or fluorescently produce a change in optical density which is sensed by a reflectometer or other optical device, the amount of light reflected from the element varying in accordance with the reaction and being indicative of the amount of a particular component present in the fluid. An example of such a reagent test slide is disclosed in U.S. Pat. No. 4,053,381, which issued on Oct. 11, 1977 to Hamblen et al., and in U.S. Pat. No. 3,992,158, which issued on Nov. 16, 1976 to Przybylowicz et al., the disclosures of which are incorporated herein by reference. A chemical analyzer which uses such reagent test slides is described in U.S. Pat. Nos. 5,089,229, 5,250,262 and 5,336,467, each of which issued on Feb. 18, 1992, Oct. 5, 1993, and Aug. 9, 1994, respectively, to Heidt et al., the disclosures of which are incorporated herein by reference.

Such typical reagent test slides must be carefully handled and stored during and prior to use in the chemical analyzer. The analyte deposited on the film of the test slide must remain free from contaminants and must not be exposed to other test slides having a different chemical reagent deposited thereon. A user of the chemical analyzer must take care in handling the reagent test slides to ensure that fingers do not touch the film portion containing the dry analyte. Additionally, once the test slide is removed from its sealed container, it should be used or otherwise loaded immediately in the chemical analyzer, as the analyte on the film portion of the test slide is now exposed to contaminants in the environment which may corrupt the tests performed by the chemical analyzer.

OBJECTS AND SUMMARY OF THE INVENTION

It is an object of the present invention to provide a holding device for retaining a plurality of reagent test slides.

It is another object of the present invention to provide a retaining clip for holding a plurality of reagent test slides in a stacked arrangement.

It is a further object of the present invention to provide a retaining clip which is adaptable for holding one or more test slides in a stacked arrangement.

It is still another object of the present invention to provide a retaining clip for holding a plurality of test slides which avoids the need for the user to handle the test slides when inserting them into a chemical analyzer.

It is yet a further object of the present invention to provide a retaining clip for a plurality of test slides which minimize the contamination of the slides from the environment or other sources.

It is yet another object of the present invention to provide a chemical reagent slide which may be held by the retaining clip for use with a chemical analyzer.

In accordance with one form of the present invention, a clip for retaining a plurality of chemical reagent test slides in a stacked arrangement includes a middle plate, a first cover plate pivotally joined to the middle plate at one end thereof, and a second cover plate joined to the middle plate at the other end thereof. The clip may be formed as an elongated unitary member, with the first cover plate and the middle plate pivotally joined together with a living hinge. The first cover plate may be pivoted with respect to the middle plate so as to be disposed in at least partial overlying relationship with the second cover plate, thereby defining a space therebetween to receive the plurality of reagent test slides in a stacked arrangement. Preferably, the second cover plate is also pivotally joined to the middle plate with another living hinge so that it, too, can also pivot with respect to the middle plate. Alternatively, the second cover plate may be fixedly joined to the middle plate and disposed at a right angle thereto.

More specifically, the retaining clip is formed preferably as a unitary member and includes first, second and third plates, each of which includes an inner surface and an opposite outer surface. First pivotal joining means interconnects the first plate and the second plate and allows the inner surface of the first plate to pivot toward the inner surface of the second plate. Second pivotal joining means interconnects the third plate with the second plate and allows the inner surface of the third plate to pivot toward the inner surface of the second plate. Alternatively, the second pivotal joining means may be omitted such that that the third plate is rigidly joined at an angle to the second plate to define a corner between the third plate and the second plate.

The retaining clip may further include restraining means coupled to at least the first plate and the third plate for restraining the plurality of reagent test slides held in a stacked arrangement between the first and third plates. The restraining means may include one or more ratchet tie fasteners and cooperating slot defining structure which defines one or more slots for receiving the fasteners, and a pawl extending into each slot for engaging the ratchet tie fastener received thereby. Alternatively, the restraining means may include a flexible band (e.g. an elastic band or o-ring) which encircles the first and third plates and the stacked arrangement of reagent test slides held between the first and third plates.

The retaining clip may include additional pivotal joining means for pivoting the inner surface of the first plate or that of the third plate to decrease the distance between the inner surface of the first plate and the inner surface of the third plate so that the retaining clip may accommodate a lesser number of reagent test slides in a stacked arrangement between the first and third plates.

A chemical reagent test slide formed in accordance with the present invention includes a frame having opposite lateral edges, and a film portion supported by the frame which is coated with a chemical reagent. Preferably, the frame is trapezoidal in shape, and each of the opposite lateral edges is formed with a recess to at least partially receive a cooperating member of a slide insertor mechanism of a chemical analyzer so that the entire stack of reagent test slides may be removed from the retaining clip and loaded onto the slide insertor mechanism of the chemical analyzer.

These and other objects, features, and advantages of the present invention will be apparent from the following detailed description of illustrative embodiments thereof, which is to be read in connection with the accompanying drawings.

BRIEF DESCRIPTION OF THE DRAWINGS

FIG. 3 is a rear isometric view of a second embodiment of a retaining clip formed in accordance with the present invention.

DETAILED DESCRIPTION OF THE PREFERRED EMBODIMENTS

Figure 1:
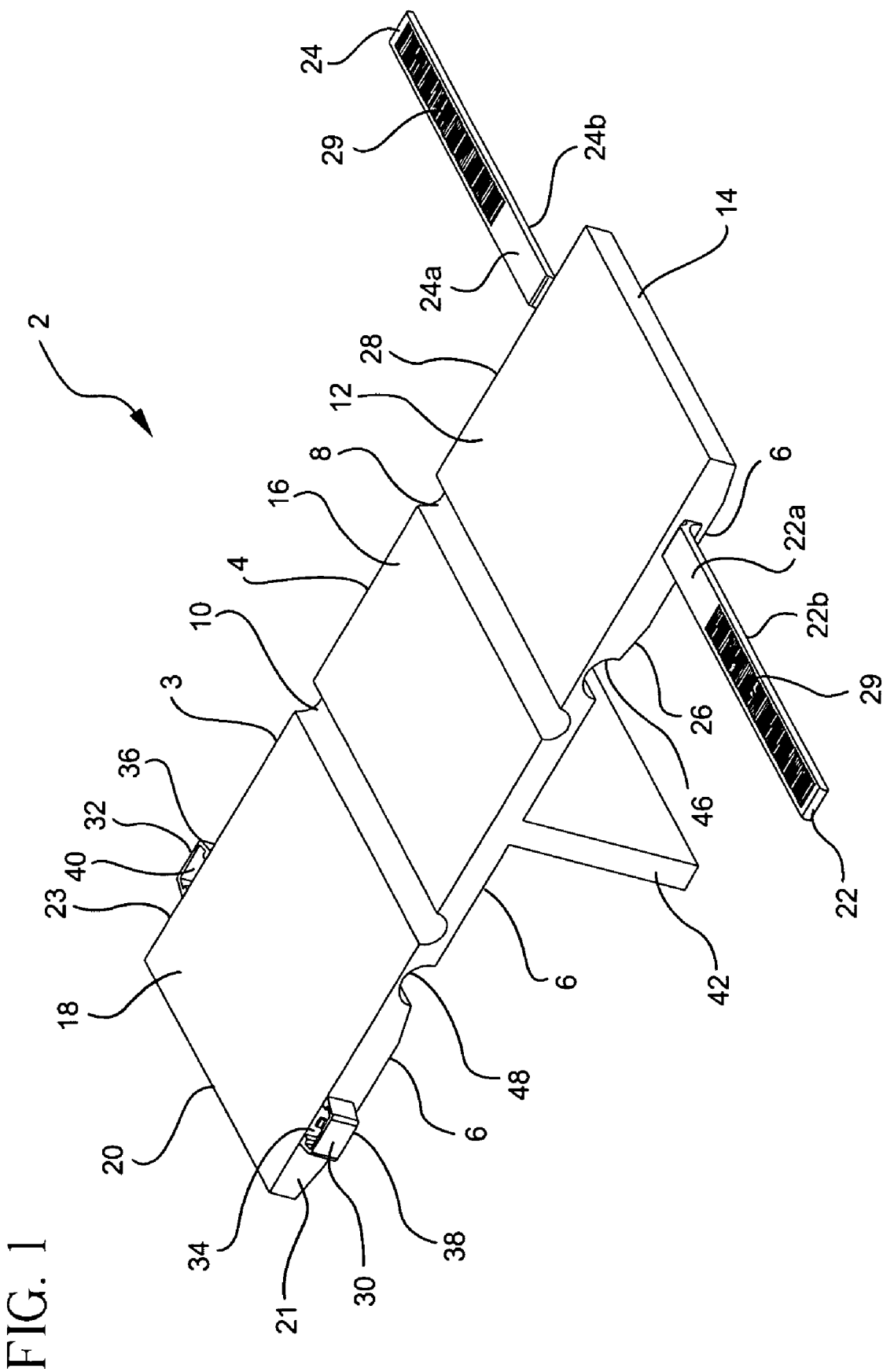
FIG. 1 is an isometric view of a first embodiment of a retaining clip formed in accordance with the present invention, the retaining clip being shown in an open, unfolded state.

Referring initially to FIG. 1 of the drawings, it will be seen that a retaining clip 2 for holding and storing a plurality of reagent test slides is preferably formed as a unitary, injection molded elongated member 3 formed of a plastic material, such as polypropylene, polystyrene, or the like. The elongated member 3 has an inner surface 4 and an opposite outer surface 6. Formed on the inner surface 4 is a first living hinge 8 and a second living hinge 10 spaced apart from the first living hinge 8 by a predetermined distance. The first and second living hinges 8, 10 define the elongated member 3 as having three segments: a first or top cover plate 12 defined between a first end 14 of the elongated member 3 and the first living hinge 8; a second or middle plate 16 defined between the first living hinge 8 and the second living hinge 10; and a third or bottom cover plate 18 defined between the second living hinge 10 and the second end 20 of the elongated member 3 which is disposed opposite the first end. The first and second living hinges 8, 10 are provided so that the elongated member 3 may be bent to take on a C-shape configuration, as shown in FIG. 2, with the top cover plate 12 overlying the bottom cover plate 18 and separated therefrom by the middle plate 16.

Figure 2:
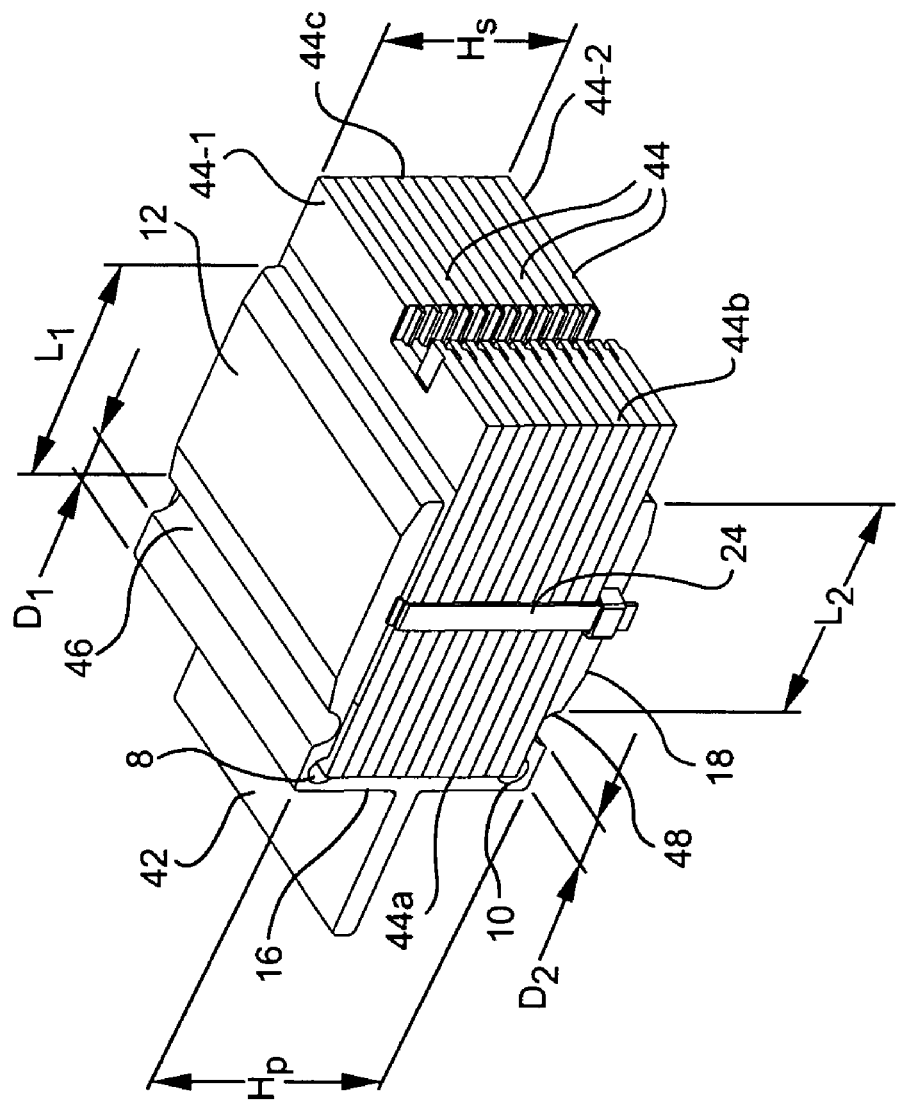
FIG. 2 is an isometric view of the retaining clip shown in FIG. 1 holding a plurality of reagent test slides.

In the particular embodiment of the retaining clip 2 shown in FIGS. 1 and 2, first and second ratchet tie fasteners 22, 24 are hingedly mounted to, with preferably living hinges 8, 10, the opposite side walls 26, 28 of either the top cover plate 12 or the bottom cover plate 18. As shown in FIGS. 1 and 2, the tie fasteners 22, 24 extend from the top cover plate 12. The tie fasteners 22, 24 are elongated members which include on at least one surface 22A, 22B thereof and 24A and 24B thereof and over at least a portion thereof a plurality of ratchet teeth 29.

First and second C-shaped members 30, 32 are mounted to and extend from opposite side surfaces of the opposite cover plate from which the ratchet tie fasteners 22, 24 extend. As shown in FIGS. 1 and 2, the C-shaped members 30, 32 extend from the side surfaces 21, 23 of the bottom cover plate 18. The first and second C-shaped members 30, 32 define with the side surfaces of the bottom cover plate 18 receiving slots 34, 36 for receiving the first and second ratchet tie fasteners 22, 24, respectively. Either formed on each inner surface 4 of the first and second C-shaped member 30, 32 or on each side surface of the bottom cover plate 18 is a pawl 38, 40 which extends into the receiving slots 34, 36 defined by the first and second C-shaped members 30, 32 and the side surfaces 21, 23 of the bottom cover plate 18. The dimensions of the receiving slots 34, 36 are such as to closely receive the first and second ratchet tie fasteners 22, 24 so that the pawl 38, 40 extending into each receiving slot 34, 36 closely engages the ratchet teeth 29 formed on the at least one surface 22A, 22B, 24A, 24B of each of the first and second ratchet tie fasteners 22, 24, as shown in FIG. 2 of the drawings. The pawls 38, 40 and ratchet teeth 29 on the first and second tie fasteners 22, 24 are oriented in such a way that they lockingly engage one another when the ratchet tie fasteners 22, 24 are inserted into their corresponding receiving slots 34, 36 and thereby prevent their disengagement.

A handle 42 for grasping by the user is formed as a tab or other protruding member which projects outwardly from and normally to the outer surface 6 of the middle plate 16. The handle 42 extends outwardly from the middle plate 16 a sufficient distance so as to be easily grasped by using one's thumb and forefinger.

The purpose of the retaining clip 2 is to retain a number of reagent test slides 44 in a stacked arrangement between the top cover plate 12 and the bottom cover plate 18, as shown in FIG. 2 of the drawings. As shown by FIG. 2, typically twelve reagent test slides (or a lesser or greater number of slides) 44 may be held in a stacked arrangement within the confines of the retaining clip 2. One edge 44A of each of the stacked reagent test slides 44 preferably abuts against the inner surface 4 of the middle plate 16, while the top cover plate 12 and bottom cover plate 18 bend at an angle at the first living hinge 8 and the second living hinge 10 to at least partially cover the top and bottom test slides in the stack. The first and second ratchet tie fasteners 22, 24 are inserted into their corresponding receiving slots 30, 32. Pressure is exerted on the top cover plate 12 and the bottom cover plate 18 with sufficient compressive force so that the stack of reagent test slides 44 is held in place between the top and bottom cover plates 12, 18, but not so tightly in order to allow the removal of one or more test slides from the stack held in place by the retaining clip 2. Each pawl 38, 40 extending into its respective receiving slot 30, 32 engages a respective one of the first and second ratchet tie fasteners 22, 24 to prevent the top cover plate 12 and bottom cover plate 18 from separating and to hold the stack of reagent test slides 44 securely therebetween. The first and second ratchet tie fasteners 22, 24 also engage opposite lateral edges 44B, 44C of the stacked reagent test slides 44 to further hold the test slides 44 in place within the retaining clip 2.

Again returning to FIG. 1 of the drawings, a third living hinge 46 and a fourth living hinge 48 may be formed respectively in the outer surface 6 of the top cover plate 12 and the bottom cover plate 18, respectively, and extending across the opposite inner surface 6 in parallel with the first living hinge 8 and the second living hinge 10. The third and fourth living hinges 46, 48 are provided to allow the top cover plate 12 and bottom cover plate 18, respectively, to be folded in on themselves to allow the retaining clip 2 of the present invention to accommodate fewer slides in the stack of slides 44 retained thereby.

In its slide-retaining configuration shown in FIG. 2, the retaining clip 2 of the present invention is designed to maintain the top cover plate 12 and the bottom cover plate 18 in a parallel relationship with respect to one another so that the top cover plate 12 and the bottom cover plate 18 lie flush with the top test slide 44-1 and the bottom test slide 44-2, respectively, in the stack of test slides 44. This flush arrangement prevents the film portions of the top and bottom slides 44-1, 44-2, which are completely covered by the top and bottom plates 12, 18, from being exposed to contaminants in the environment including, for example, contaminants from user handling. The slides in the stack 44 between the top and bottom slides 44-1, 44-2 are protected from the environment by their adjacent slides in the stack. The width and depth of the top cover plate 12 and the bottom cover plate 18 are such as to preferably completely cover the film portion of the reagent test slides 44 and to be sufficient in dimensions to securely hold the stack of test slides 44 in place within the clip 2.

Stated in other words, the dimensions of the retaining clip 2 shown in the drawings is such as to accommodate preferably twelve reagent test slides 44 for its maximum capacity (although the retaining clip 2 may be dimensioned to accommodate any desired number of reagent test slides 44 disposed in a stack). As shown in FIG. 2, the middle plate 16 is dimensioned between the first and second living hinges 8, 10 to have a height Hp which is equal to the height Hs of twelve reagent test slides 44 arranged in a stack. However, the same retaining clip 2 may accommodate fewer test slides by having the top cover plate 12 fold at the third living hinge 46 inwardly toward the inner surface of the middle plate 16, and the bottom cover plate 18 similarly fold at the fourth living hinge 48 inwardly toward the inner surface of the middle plate 16. Depending upon the distance D1 between the first and third hinges 8, 46 and the distance D2 between the second and fourth hinges 10, 48, respectively, the retaining clip 2 of the present invention may accommodate one or more test slides between the top cover plate 12 and the bottom cover plate 18, while still maintaining the parallel relationship between the top and bottom cover plates 12, 18. Furthermore, with the top and bottom cover plates 12, 18 folded at the third and fourth living hinges 46, 48, the top and bottom cover plates 12, 18 have a length L1, L2 measured from the third and fourth living hinges 46, 48 to the free ends 14, 20 of the top and bottom cover plates 12, 18 to entirely cover the film portion 73 (FIG. 7) of the test slides 44 to prevent their contamination from the environment. Additionally, the third and fourth living hinges 46, 48 allow the top cover plate 12 and bottom cover plate 18 to lie flush against the top and bottom slides 44-1, 44-2, respectively, in the stack of slides 44 even if fewer than the maximum number of test slides are held in place by the retaining clip 2.

A second embodiment of a retaining clip formed in accordance with the present invention is illustrated by FIGS. 3-6 of the drawings. In this version, retaining clip 50 is comprised of a third or bottom cover plate 51 which is fixedly mounted at preferably a right angle to a second or middle plate 52 and acts as a lower shelf for mounting the stack 44 of reagent test slides thereon. As shown in FIG. 3, the bottom cover plate 51 may include on the outer surface 51A thereof one or more stiffening ribs 53 to provide extra rigidity thereto and to prevent flexing of the bottom cover plate 53. A first or top cover plate 55 is pivotably secured to the middle plate 52 with a living hinge 54, such as the first living hinge 8 of the previous embodiment shown in FIGS. 1 and 2 of the drawings. The top cover plate 55 also includes another living hinge 56 formed on its inner surface 55B, similar to the third living hinge 46 formed in the retaining clip shown in FIGS. 1 and 2, to accommodate a lesser number of test slides in the stack of test slides 44.

Figure 4B:
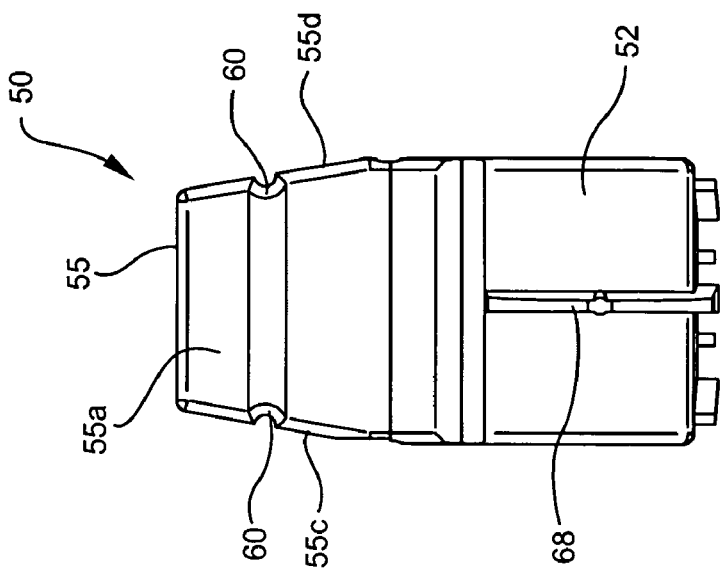
FIG. 4B is a rear view of the retaining clip of the present invention shown in FIG. 3
Figure 4A:
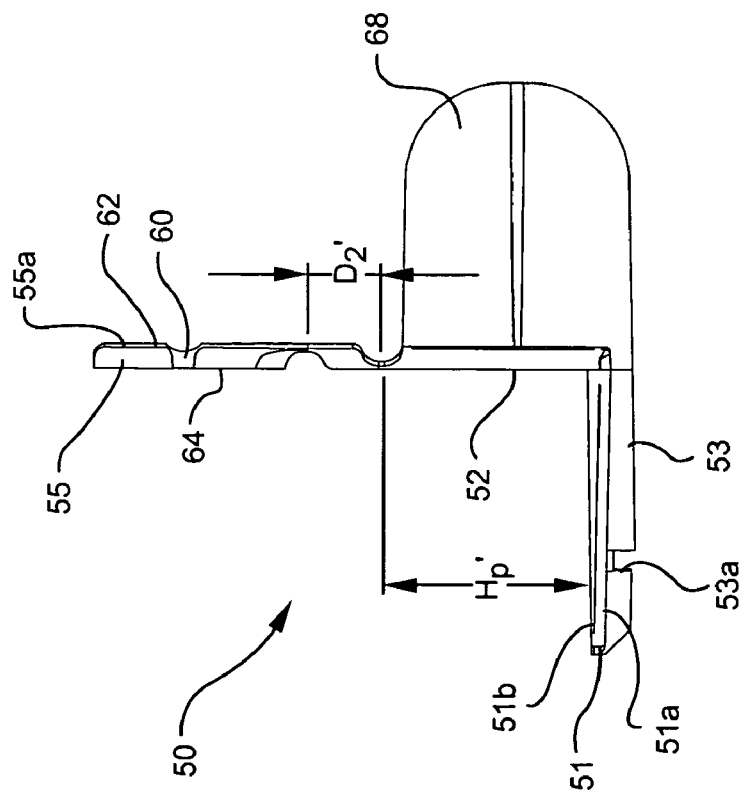
FIG. 4A is a side view of the retaining clip of the present invention shown in FIG. 3.
Figure 4C:
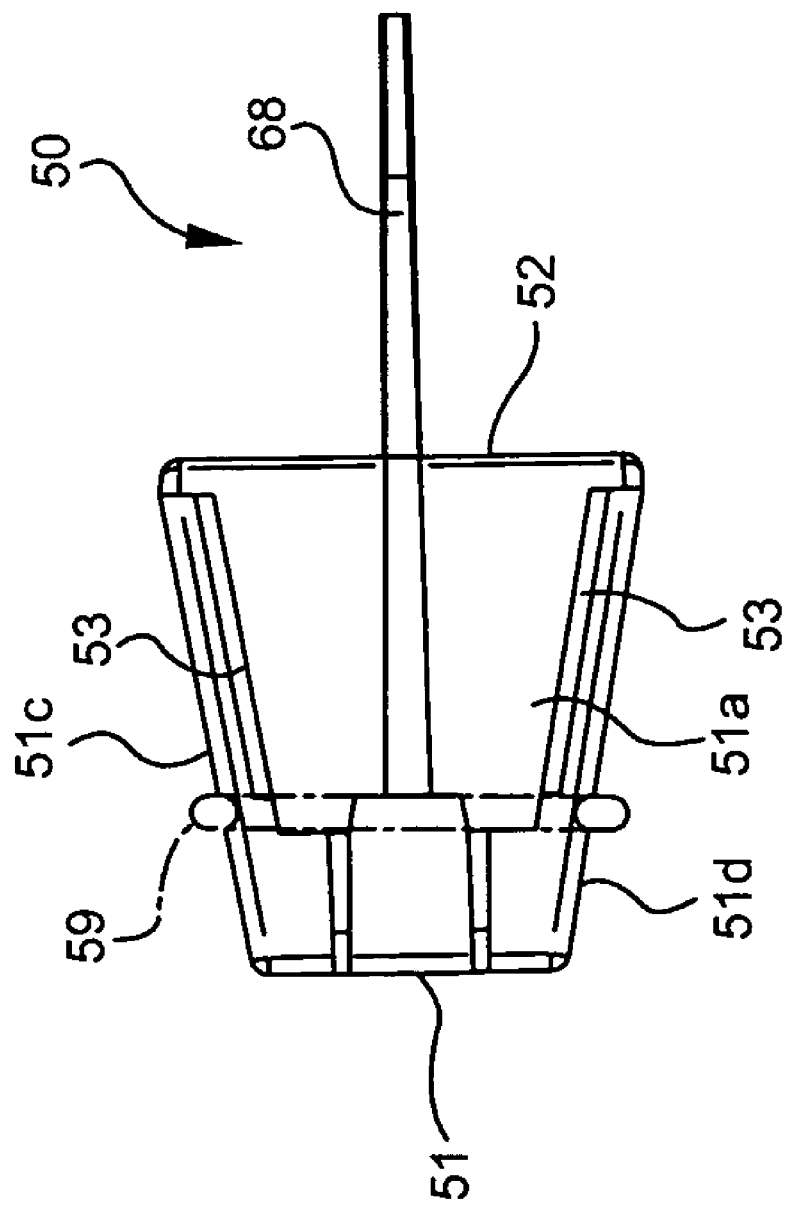
FIG. 4C is a bottom view of the retaining clip of the present invention shown in FIG. 3.
Figure 5:
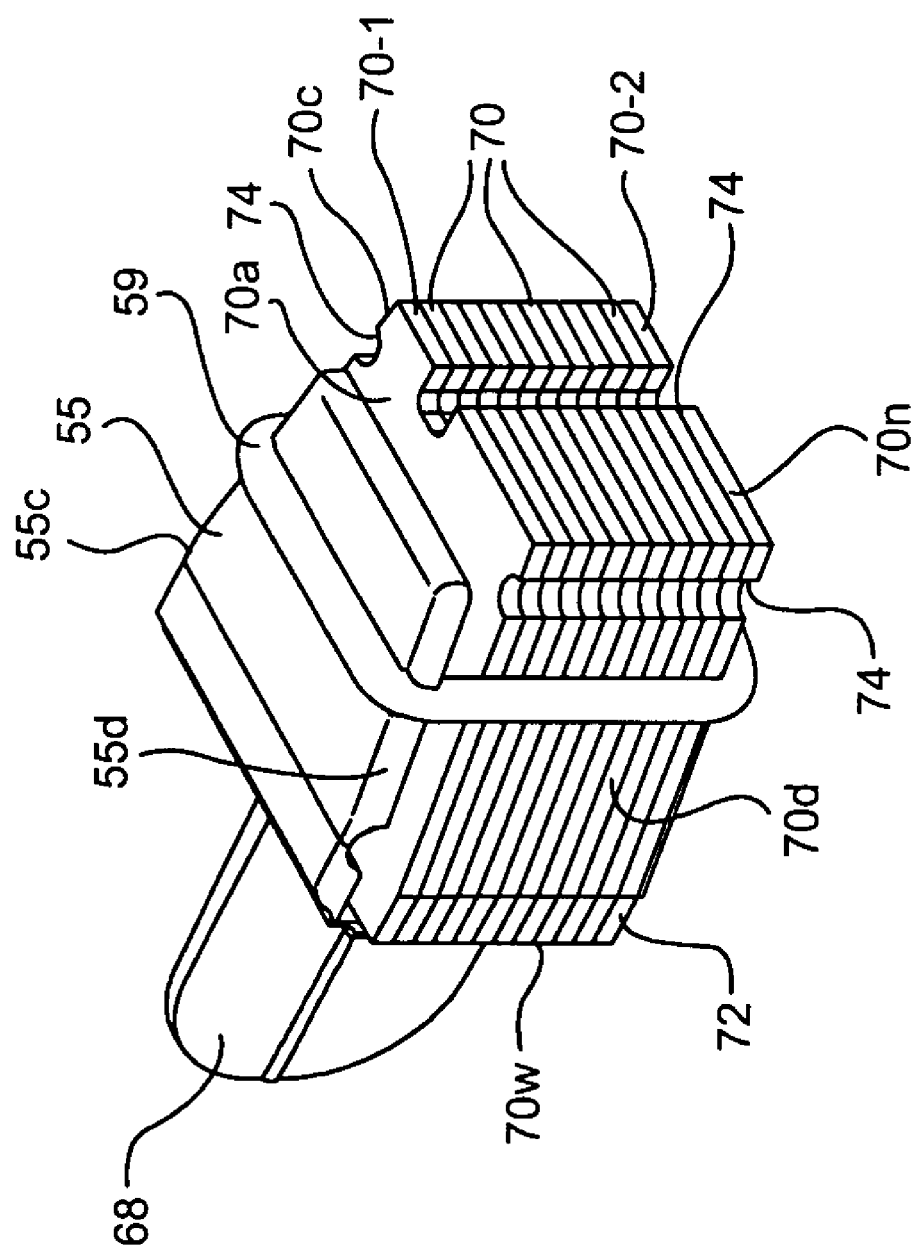
FIG. 5 is a front isometric view of the retaining clip shown in FIGS. 3 and 4 and shown holding a plurality of reagent test slides.

As shown in FIGS. 4-5, the dimension Hp' is the dimension or height of the middle plate 52 which corresponds to the maximum height of the stack of reagent test slides 70 which can be accommodated. The dimension D2' is the distance between the first living hinge 54 and the second living hinge 56. Depending upon the size of D2', a corresponding lesser number of slides 70 can be accommodated.

Figure 6:
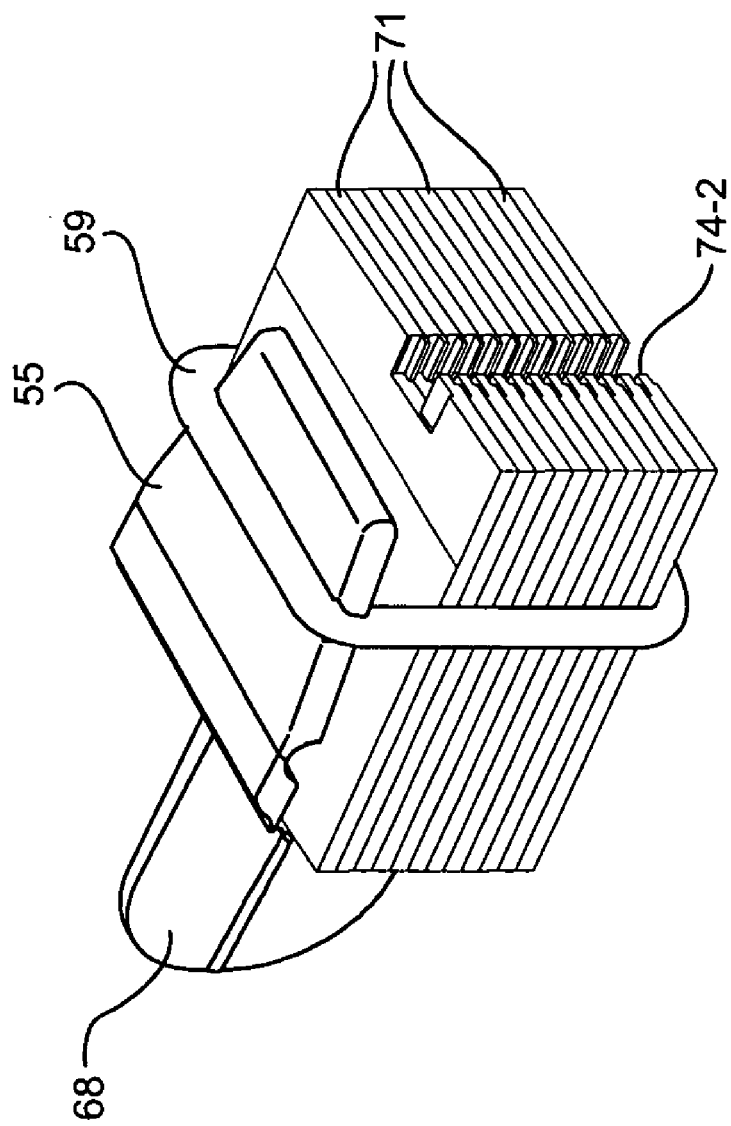
FIG. 6 is a front isometric view of the retaining clip shown in FIG. 5 and shown holding a plurality of different reagent test slides from those shown in FIG. 5.

Although the version of the retaining clip 50 of the present invention shown in FIGS. 3-6 can include ratchet tie fasteners 22, 24 and C-shaped receiving slot members 30, 32 such as in the embodiment shown in FIGS. 1 and 2, even more preferably it includes, as shown in FIGS. 5 and 6, a flexible band 59, such as an elastic band or o-ring, which surrounds the outer surfaces 51a, 55a of the top and bottom cover plates 51, 55 and the stack of reagent test slides 70 held in place therebetween, as shown in FIGS. 5 and 6 of the drawings. For this purpose, a first groove 60 is formed in the top outer surface 55a of the top cover plate 55 and, preferably, in opposite side edges 55c, 55d, 51c, 51d of each of the top and bottom cover plates 55, 51, to allow the flexible band 59 to be seated therein and retained in place thereby. Notches 53a can also be formed in ribs 53 for additional security of flexible band 59. As with the first embodiment, the retaining clip 50 shown in FIGS. 3-6 includes an elongated handle 68 extending outwardly from the outer surface 52A of the middle plate 52 so as to allow the user to firmly grasp the retaining clip 50 without touching either the test slides 70 or the top or bottom cover plates 55, 51 and exerting pressure on the stacked test slides 70 which would prevent or impede their removal from the retaining clip 50 during insertion of each test slide 70 in the chemical analyzer (not shown).

As shown in FIGS. 5 and 6, the top and bottom cover plates 55, 51 at least partially over the test slides 70 retained thereby, and preferably entirely cover the film portion 73 of the top and bottom test slides 70-1 and 70-2 in the stack to prevent their exposure to contaminants in the environment prior to the test slides 70 being loaded into the chemical analyzer, as is the case with the first embodiment shown in FIGS. 1 and 2. Also, the top cover plate 51 may be folded inwardly towards the middle plate 52 to accommodate fewer test slides in the stack 70, while still lying flush against the upper surface 70A of the top slide in the stack and still covering the film portion of the top slide 70-1.

In the embodiment shown in FIG. 5 of the drawings, the top and bottom cover plates 55, 51 are preferably trapezoidal in shape. This shape is particularly provided to accommodate and conform to the particular shape of trapezoidal test slides 70 also formed in accordance with the present invention. The trapezoidal test slides 70 include a wider outer edge 70W and a narrower, opposite inner edge 70N, and opposite lateral edges 70C, 70D which mutually converge toward the narrower inner edge 70N. Preferably formed in the lateral edges 70C, 70D of the test slides 70, near the narrower inner edge 70N, are recesses 74 which are preferably angled inwardly of each test slide toward the narrower inner edge 70N. The purpose of these recesses 74 is to allow the entire stack of reagent test slides 70, held in place by the retaining clip 50, to be inserted into a slide injector mechanism of the chemical analyzer, which injector mechanism includes opposite, preferably dovetailed, vertical members (not shown) which are parallel to and spaced apart from one another a distance which corresponds to the width of each test slide measured laterally in proximity to the opposite recesses 74. Each vertical member on the injector mechanism preferably includes a resilient retainer (not shown) which is received by a corresponding one of the lateral recesses 74 on the test slides 70. The retaining clip 50 of the present invention, carrying a stack of reagent test slides, is grasped by the user at the handle 68 and placed onto the injector mechanism of the chemical analyzer such that the opposite lateral edges 70C, 70D of the slides are facing the parallel, vertically upstanding members of the injector mechanism. The retaining clip 50, with its stack of reagent test slides 70, is pushed forward onto the injector mechanism such that the opposite resilient retainers on the vertical members engage and are received by the recesses 74 formed in the test slides 70. Alternatively, because the vertical members of the injector mechanism may be free standing, the entire stack of slides held by the retaining clip may be inserted onto the inserter mechanism from above the members. It should be noted that since each test slide 70 has the same configuration, the recesses 74 of the test slides are aligned as grooves on opposite sides of the stack 70. The resilient retainers of the vertical members of the injector mechanism are received by these grooves defined by the recesses 74 and hold the entire stack of reagent test slides 70 in place between the vertical members. The user now firmly grasps the retaining clip 2, 50 of the present invention and pulls backwardly, away from the injector mechanism and the upstanding, vertical members. The flexible band 59 has sufficient resiliency to allow the entire stack to be longitudinally displaced from between the top and bottom cover plates and removed from the retaining clip. The grooves 60 and notch 53a formed in the top and bottom cover plates retain the flexible band 59 in place on the retaining clip 50 while the stack of reagent test slides 70 is being removed therefrom. Accordingly, the retaining clip 2, 50 of the present invention allows an entire stack of reagent test slides 44, 70 to be inserted in the chemical analyzer without the need for the user to handle individual test slides. The retaining clip 2, 50 of the present invention facilitates loading test slides into the chemical analyzer and minimizes any possible contamination from the user touching the film portion of the test slides or from the environment.

The particular injector mechanism described above is disclosed with particularity in U.S. Provisional Application Ser. No. 60/526,884, filed on Dec. 4, 2003, and entitled "Reagent Test Slide Injector Mechanism Having a Scotch Drive and Rotatable Turntable Having a Geneva Drive for a Chemical Analyzer," the disclosure of which is incorporated herein by reference. Nevertheless, to facilitate an understanding of the invention, particularly with respect to how the chemical reagent test slides held by the retaining clip cooperate with the slide injector mechanism, a preferred form of the chemical reagent test slides and the slide injector mechanism is described below.

Figure 7:
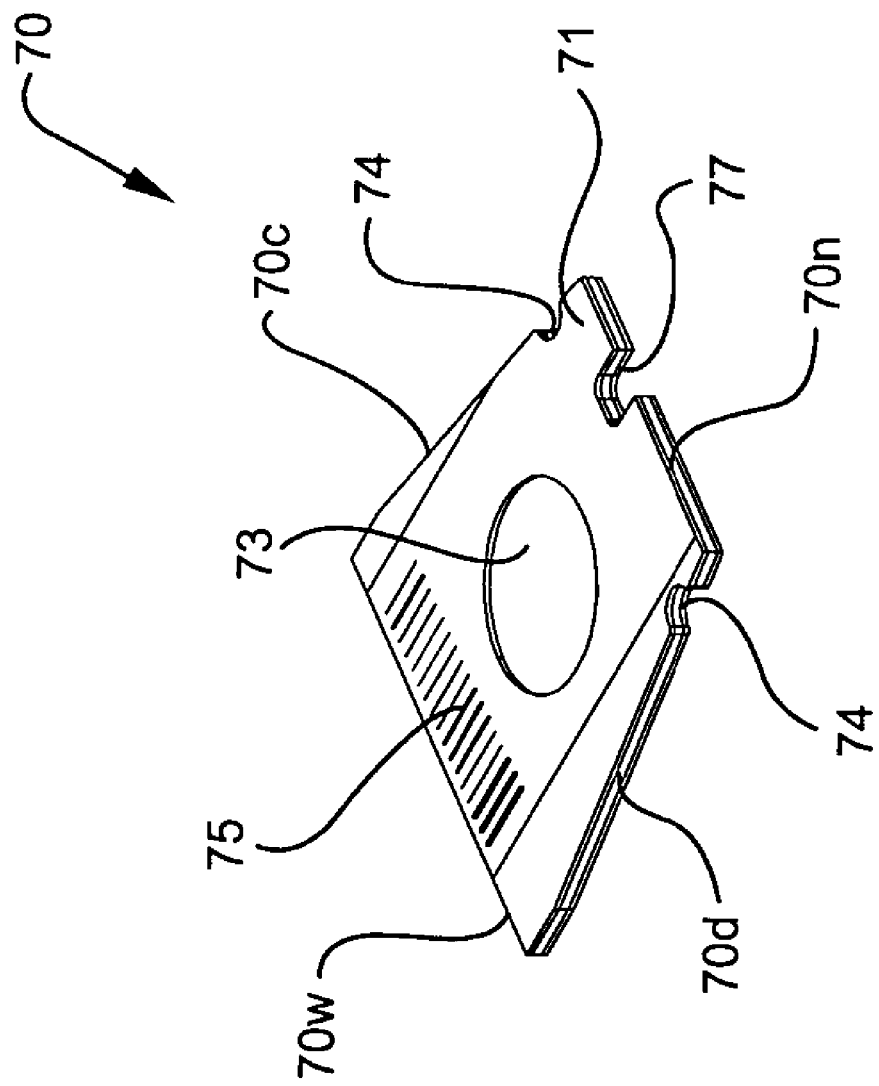
FIG. 7 is a top isometric view of a reagent test slide formed in accordance with the present invention.

The particular structure of the chemical reagent test slides described herein, alone or in combination with the retaining clip, is an important aspect of the overall invention. The test slides 70 may have a frame 71 which is rectangular in shape, such as those shown in FIG. 6 of the drawings, but, in accordance with the present invention, are preferably trapezoidal in shape, as shown in FIG. 7. The frame surrounds and supports a circular film portion 73 situated interiorly of the edges of the frame, which film portion 73 is coated with an analyte or chemical reagent, as is well known in the art. Common test slides used in biological fluid analysis include, for example, one for a calcium (Ca) test, another for an aspartate transminase (AST) test, and a third for a glucose (Glu) test.

An advantage of having reagent test slides 70 which are trapezoidal in shape is that this shape allows a greater number of test slides to be mounted circumferentially, side-by-side, on a rotatable turntable (not shown) of a chemical analyzer, such as turntable 50 disclosed in the aforementioned Heidt et al. patents, modified to accept trapezoidally shaped slides. Furthermore, the trapezoidal shape of the reagent test slides 70 ensures that the test slides will be properly oriented when they are loaded on the retaining clip or inserted onto the rotatable turntable.

Also, each test slide 70 preferably includes information 75, imprinted on one side of the frame 71 and preferably situated along the larger (i.e., base) side 70W of the slide frame. The information 75 can include, for example, slide type, manufacturing date, expiration date, lot number and/or calibration information. The information can be in any suitable readable form, such as bar code or universal product code (UPC). The information 75 also helps a user orient the test slides properly during insertion into the retaining clip to prevent the slides from being inserted upside down.

The test slides may further include a notch 77 formed in one of its edges, such as the narrow inner edge 70N, which notch may be offset from the longitudinal centerline of the slide toward one lateral edge 70C or the other lateral edge 70D. The notch 77 may be used to facilitate the orientation and loading of the slides onto a slide insertor mechanism of a chemical analyzer, and may cooperate with and receive a projection (not shown) of the slide insertor mechanism which ensures the slide's proper orientation on the insertor mechanism.

It should be further noted that the top and bottom cover plates 12, 18, 55, 51 are preferably dimensioned so that they entirely cover the film portion 73 of the top and bottom end slides in the stack, but also have a width which is less than the width of the test slides measured across the slides between the recesses 74 formed in the opposite lateral edges 70C, 70D so that at least portions of the lateral edges of the slides bearing the recesses 74 extend beyond the lateral sides of the top and bottom cover plates 12, 18, 55, 51 to expose the recesses 74 and so that the recesses 74 may cooperate with and receive portions of the upstanding vertical members of the slide injector mechanism while the test slides are still retained by the retaining clip.

Figure 8:
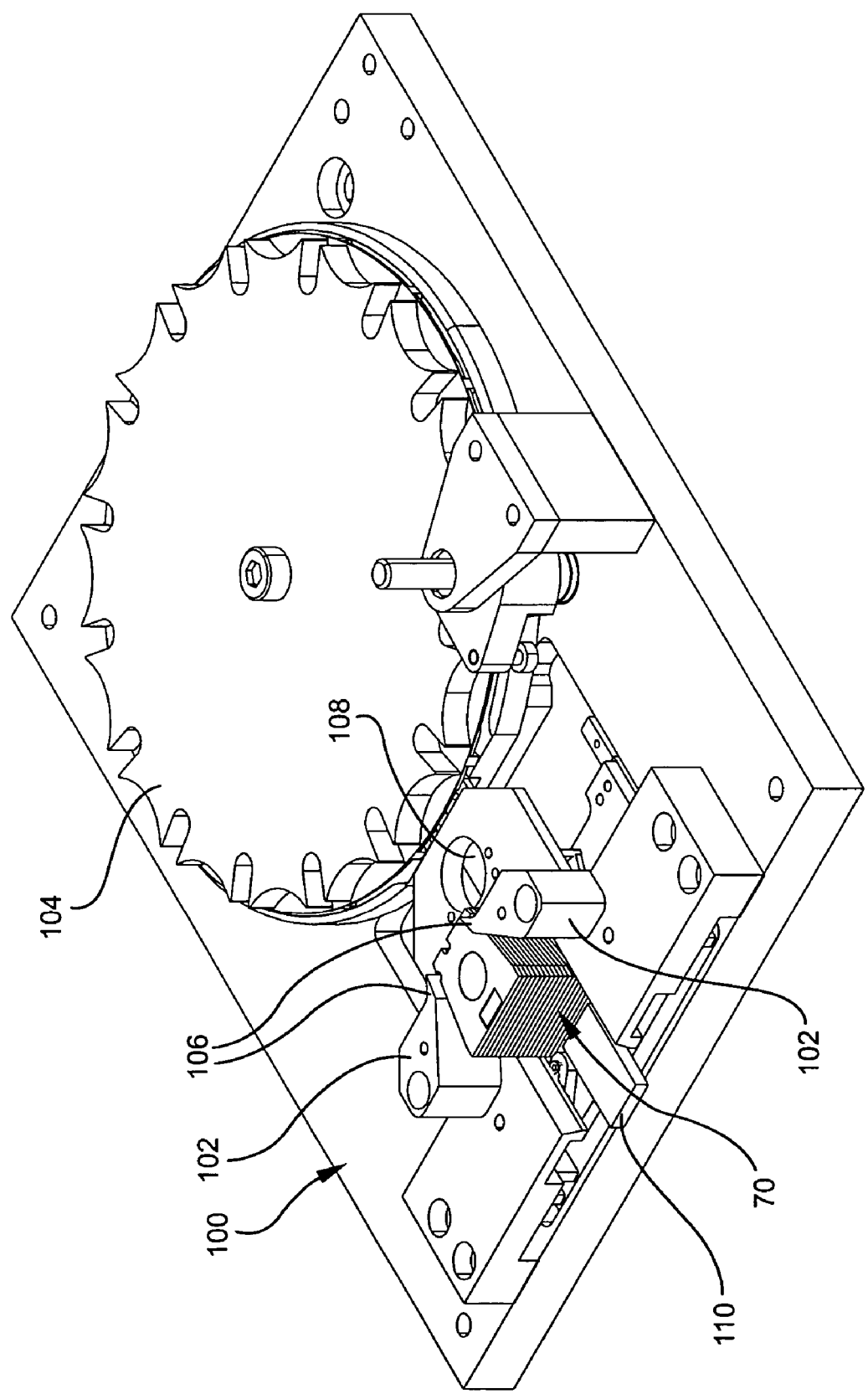
FIG. 8 is a top perspective view of a slide injector mechanism and rotatable turntable for a chemical analyzer, formed in accordance with the present invention.
Figure 9:
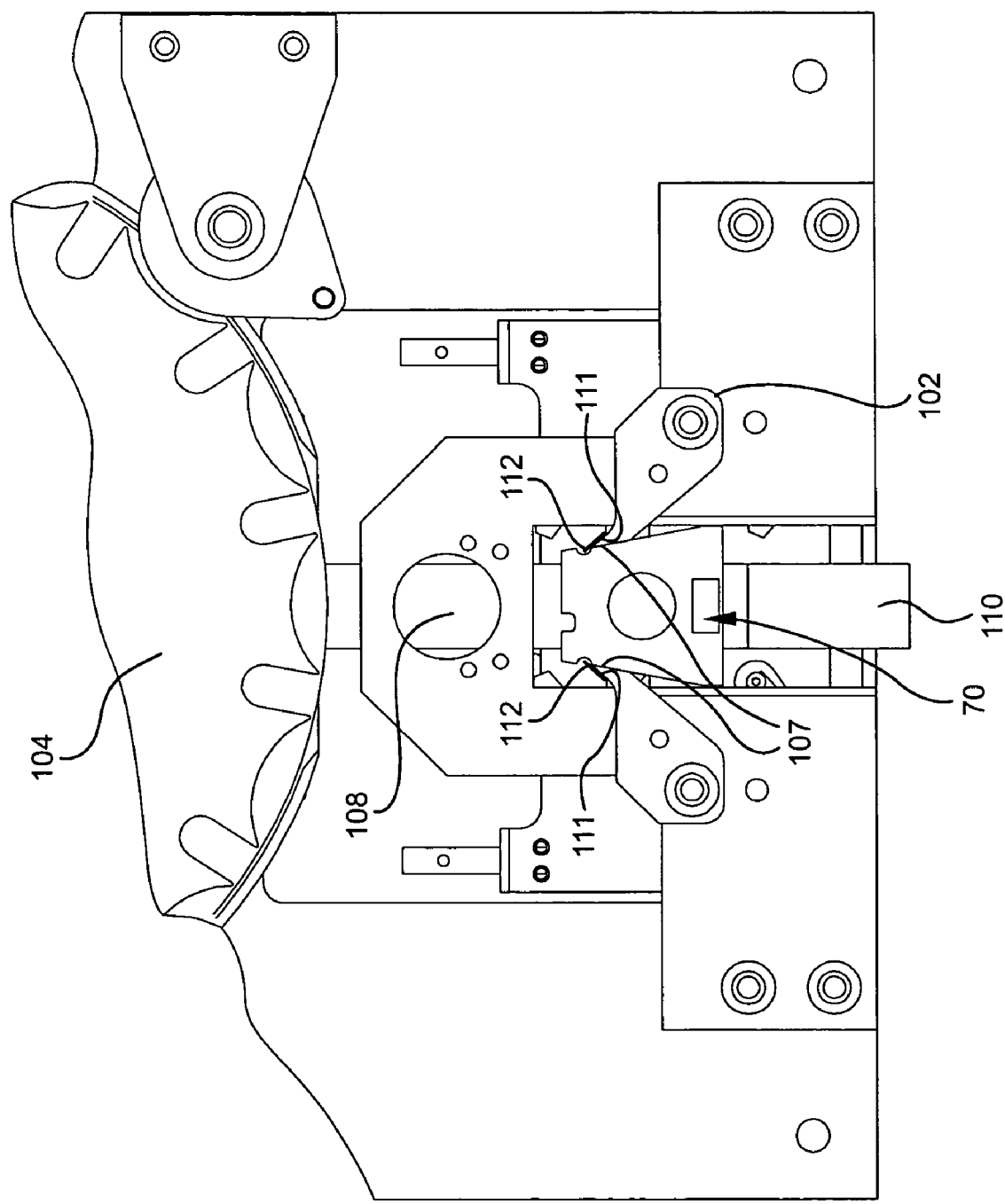
FIG. 9 is a top plan view of the slide injector mechanism of the present invention shown in FIG. 8.

FIGS. 8 through 9 show in greater detail a test slide injector mechanism 100 formed in accordance with the present invention and which includes structural components that interface with the test slides 70 to help remove the slides, in a stacked arrangement, from the retaining clip. As shown in FIG. 8, the slide injector mechanism 100 includes a pair of spaced apart upstanding blocks 102 between which a stack of reagent test slides 70 is placed. One end of each block nearest the rotatable turntable 104 is formed with an outwardly beveled, or dovetailed, projection 106, the projection 106 on one block 102 facing the projection 106 on the other in mirrored symmetry and spaced apart from one another a predetermined distance. The exposed beveled face 107 on each projection 106 is angled to conform to the particular angle of the lateral edges 70C, 70D of the trapezoidally-shaped reagent test slides 70 so that the front portions of the test slides, loaded as a stack onto the slide injector mechanism, will lie between the two projections 106. The projections 106 maintain the position of the stack of test slides 70 loaded into the injector mechanism 100. Individual test slides 70 taken from the bottom of the stack of slides will be sequentially moved by the injector mechanism, one at a time, to a spotting position 108 in alignment with a sample metering device (not shown) and, subsequently after being spotted, will be loaded onto the rotatable turntable 104. The actual mechanism for moving the individual test slides from the spotting position to the rotatable turntable in not described herein, as any number of mechanisms, such as a solenoid driven, reciprocatingly movable push rod or plate 110 that engages the slide 70, may be employed as would be well known to one skilled in the art.

The beveled projections 106 on the blocks 102 prevent the stack of test slides 70, other than the lower most slide in the stack, from being moved forward. Even more preferably, each projection 106 may include a slide retainer clip 112 (see FIG. 9) which is mounted, by adhesive or the like, to a second sloped surface 111 of each projection 106. The slide retainer clips 112 may be formed from a resilient plastic or metal sheet material and extend slightly beyond the angled edge defined by the first beveled surface 107 and the second sloped surface 111 of each projection 106.

As described previously, the trapezoidally-shaped reagent test slides 70 preferably include recesses 74 which are formed in the lateral edges 70C, 70D of the test slides, near the narrower inner edge 70N, which recesses 74 may be angled inwardly of each test slide toward the narrower inner edge. The purpose of these recesses 74 is to permit the slide retainer clips 112 mounted on each projection to be resiliently received therein. The cooperation of the slide retainer clips 112 and the recesses 74 formed in the reagent test slides 70 further maintain the position of the stack of test slides in the slide injector mechanism 100. Even more preferably, the cooperation of the slide retainer clips 112 and the test slide recesses 74 allow an entire stack of slides to be inserted into the slide injector mechanism in a load position by using the retaining clip described previously.

The user may conveniently use the retaining clip of the present invention, which includes a plurality of reagent test slides pre-arranged in a stack, with the recesses 74 formed on the lateral edges of the slides 70 exposed. The user grasps the handle of the retaining clip and inserts the entire stack of slides 70 held thereby onto the slide injector 100 between the two blocks-102, and pushes forward until the lateral edges 70C, 70D of the slides in the stack engage the beveled edges 107 of the block projections 106. The resilient retaining clips 112 formed on the projections will ride up against the front portions of the lateral edges 70C, 70D of the slides and snap into the test slide recesses 74, due to the clips' resiliency, and hold the stack of test slides 70 in place between the opposite blocks 102, with the front most portions of the lateral edges of the slides residing against the beveled surfaces 107 of the projections 106. The user will hear an audible click from the resilient retaining clips 112 snapping into the slide recesses 74 and will know that the test slides, still held by the retaining clip, are properly mounted in place on the injector mechanism 100. The user may now pull backward on the handle of the retaining clip, and the entire stack of slides 70 held thereby will be removed from the retaining clip, as they are now held in place on the injector mechanism 100. It is also envisioned that the slides 70 may be unloaded from the retaining clip onto the slide injector mechanism 100 from atop the blocks 102, with the grooves in the stack defined by the slide edge recesses 74 slidably receiving the resilient retaining clips 112, as described previously herein.

The cooperation between the retaining clip of the present invention and the structure of the injector mechanism allows an entire stack of reagent test slides to be easily and quickly loaded into the chemical analyzer. There is no need for individual slides to be handled by the user or loaded individually onto the injector mechanism. The height of the opposing blocks 102, and their projections 106, are such that they may receive a stack of reagent test slides 70, or multiple stacks of slides, loaded by the user with one or more retaining clips, such that the height of the stack of slides does not exceed the height of the blocks and their projections.

It should be understood that the retaining clip 50 of the second embodiment, with a trapezoidal shape to the top and bottom cover plates 55, 51, may still accommodate the square or rectangular reagent test slides 44 described previously for the first embodiment, and as shown in FIG. 6. The trapezoidally-shaped top and bottom cover plates 55, 51 are preferably dimensioned, in a manner obvious to those skilled in the art based on the previous disclosure regarding the dimensions Hp, Hs, D1, D2, L1 and L2, to still cover the film portion of such rectangularly-shaped test slides 44, and still lie flush against the top and bottom test slides in the stack of test slides 44.

It should be further realized that either of the embodiments shown in FIGS. 1-6 may be used to load rectangular or square slides 44 onto an injector mechanism in a chemical analyzer either individually or as a stack of slides. The square or rectangular slides 44 may include recesses 74-2 similar to those shown as recesses 74 in FIG. 5 of the drawings, which cooperate with projecting members or other structure of the injector mechanism of the chemical analyzer so that the entire stack of slides 44 or 70, or individual test slides from the stack, held by the retaining clip 2, 50 of the present invention may be removed from the retaining clip 2, 50 with the user only grasping the handle 42, 68 of the retaining clip 2, 50 and not touching or handling the test slides 44, 70 of the stack.

There are a number of advantages with the retaining clip of the present invention. There are no dividers between each test slide in the stack. Therefore, the retaining clip of the present invention may handle a greater density of test slides in a smaller space. Alternatively, "dummy" slides could be used to separate slides that may cross-contaminate. It is preferred, however, that the same or compatible dry analyte slides are used in the stack to prevent cross-contamination and mixing of dry analytes between adjacent test slides.

Also, as previously mentioned, the top and bottom cover plates of the retaining clip preferably cover the film portion of the top and bottom slides in the stack. The middle slides are, of course, protected from the environment by the top and bottom slides and their next adjacent slides in the stack. This minimizes air exposure and contamination of the slides and increases their shelf life. It is preferred, however, that the retaining clip with a pre-mounted stack of slides held in place is encapsulated in an air tight (low permeability) plastic or foil enclosure.

The slide retaining clip of the present invention is easy to mold by injection molding or other methods. This decreases the cost of manufacture of the retaining clip. Also, because the retaining clip of the present invention can accommodate different height stacks in one retaining clip, fewer retaining clips of different sizes are required, which also decreases the cost of the molding process.

The retaining clip of the present invention allows a single slide from the stack, or the entire stack, to be loaded into the chemical analyzer. Only one motion is required, which simplifies the loading process and minimizes the loading time, which has the further benefit of minimizing any likelihood of exposure of the test slides to contaminants in the environment. Further, there is no need for the user to handle individual test slides, which further minimizes the chance that the film portion may be inadvertently touched and contaminated.

Because the top cover plate 55 in the second embodiment, and the top and bottom cover plates 12, 18 in the first embodiment described previously, may be folded inwardly to accommodate fewer test slides in the stack, the top and bottom cover plates exert a uniform and constant sealing force on the test slides within the stack. This increases the shelf life of the test slides prior to their use.

Also, because either the top or bottom or both top and bottom cover plates are movable relative to each other, stacks of varying number of test slides may be accommodated by a single retaining clip, and fewer retaining clips to accommodate the required number of test slides for a chemical analyzer are required which, of course, leads to the need for fewer stock keeping units (sku's) in the manufacturer's database.

Since the retaining clips of the present invention may accommodate stacks of varying number of test slides, the retaining clips may be used with stacks of different dry analyte slides. In other words, certain tests may require more of one reagent type of test slide than another reagent type. The same retaining clip may be used to accommodate eight calcium test slides or twelve ammonia test slides or a mix of various chemistries, for example. The first stack of calcium test slides may be loaded onto the injector mechanism of the chemical analyzer from the first retaining clip, and the second stack of ammonia test slides may be loaded on top of the first stack on the injector mechanism from the second retaining clip. This allows batching of test slides in the chemical analyzer without the need for the user to handle test slides individually. Thus, the retaining clip is perfectly adaptable to accommodate different sized stacks of test slides.

Also, the particular trapezoidal shape of the test slides, as well as the conforming shape of the retainer clip top and bottom cover plates, permit individual slides or the entire stack of slides to be removed from the retaining clip with ease. The trapezoidal shape of the test slides, with the recesses formed in the side edges of the test slides, cooperate with and allow the injector mechanism to unload the slides from the retaining clip and hold the test slides securely in place in a stack. Furthermore, there is a noticeable audible click (from the resilient retainers snapping into the slide recesses) when the test slides are removed from the retaining clip and properly secured on the injector mechanism, which alerts the user that proper loading of the test slides on the chemical analyzer has occurred. The particular trapezoidal shape of the test slides allows a greater number of test slides to be loaded on a rotatable turntable of the chemical analyzer planarly, in a side-by-side configuration, such as shown in the previously mentioned Heidt et al. patents.

The retaining clip of the present invention is also easy to manufacture, as there are no critical dimensions required, other than ensuring that the length of the top and bottom cover plates fully cover the film portion of the test slides for the preferred form of the invention. Furthermore, the built-in handle facilitates the use and handling of the test slides.

The retaining clip of the present invention is a disposable unit which may be recycled. It further may include an RFID (radio frequency identification) or bar code situated in several suitable locations, including its top and bottom cover plates, or more preferably, on the handle thereof, to identify the type of test slides which are being loaded onto the chemical analyzer. The RFID or bar code is sensed by the chemical analyzer, which provides such information to the electronic circuit and software of the analyzer.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. In combination:
   a plurality of dry chemical reagent test slides disposed in a stacked arrangement, each reagent test slide of the plurality of reagent test slides including a frame having opposite lateral edges, the frame being trapezoidal in shape, and wherein each of the opposite lateral edges has formed therein a recess, and a film portion supported by the frame and being coated with a chemical reagent; and
   a retaining clip for retaining the plurality of reagent test slides in the stacked arrangement, the retaining clip including:
   a middle plate;
   a first cover plate pivotally joined to the middle plate; and
   a second cover plate joined to the middle plate, the first cover plate being pivotal with respect to the middle plate so as to be disposed in at least partial overlying relationship with the second cover plate and thereby defining a space therebetween to receive the plurality of reagent teat slides in the stacked arrangement.

2. A combination as defined by claim 1, wherein the retaining clip further comprises:
   a first living hinge, the first living hinge pivotally joining the middle plate to the first cover plate.

3. A combination as defined by claim 2, wherein the retaining clip further comprises:
   a second living hinge, the second living hinge being formed on the first cover plate, the first cover plate being pivotal at the second living hinge thereby decreasing the space between the first cover plate and the second cover plate for receiving the plurality of reagent test slides in the stacked arrangement.

4. A combination as defined by claim 1, wherein the second cover plate of the retaining clip is fixedly joined to the middle plate of the retaining clip at substantially a right angle thereto.

5. A combination as defined by claim 1, wherein the second cover plate of the retaining clip is pivotally joined to the middle plate of the retaining clip, the first and second cover plates of the retaining clip being pivotal with respect to the middle plate of the retaining clip so as to be disposed in at least partial overlying relationship with each other.

6. A combination as defined by claim 1, wherein the stacked arrangement of the plurality of reagent test slides includes an end reagent test slide, and wherein at least one of the first cover plate of the retaining clip and the second cover plate of the retaining clip is dimensioned to entirely cover the film portion of the end reagent test slide of the stacked arrangement.

7. In combination:
   a plurality of dry chemical reagent test slides disposed in a stacked arrangement, each reagent test slide of the plurality of reagent test slides including a frame having opposite lateral edges, the frame being trapezoidal in shape, and wherein each of the opposite lateral edges has formed therein a recess, and a film portion supported by the frame and being coated with a chemical reagent; and a retaining clip for retaining the plurality of reagent test slides in the stacked arrangement, the retaining clip comprising:

a first cover plate;

a middle plate; and a second cover plate, the first cover plate being disposed in at least partial overlying relationship with the second cover plate and thereby defining a space therebetween to receive the plurality of reagent test slides in the stacked arrangement, the first cover plate and the second cover plate being joined to the middle plate.

8. A combination as defined by claim 7, wherein the stacked arrangement of the plurality of reagent test slides includes an end reagent test slide, and wherein at least one of the first cover plate of the retaining clip and the second cover plate of the retaining clip is dimensioned to entirely cover the film portion of the end reagent test slide of the stacked arrangement.

9. A retaining clip for retaining a plurality of reagent test slides in a stacked arrangement, the retaining clip comprising:

a first plate having an inner surface and an outer surface;

a second plate having an inner surface and an outer surface;

a third plate having an inner surface and an outer surface;

first pivotal joining means for pivoting the inner surface of the first plate towards the inner surface of the second plate;

second pivotal joining means for pivoting the inner surface of the third plate towards the inner surface of the second plate, the first pivotal joining means for pivoting the inner surface of the first plate and the second pivotal joining means for pivoting the inner surface of the third plate allowing the inner surface of the first plate and the inner surface of the third plate to at least partially face each other upon pivoting, the inner surface of the first plate and the inner surface of the third plate being separated by a predetermined distance to define a space therebetween for receiving the plurality of reagent test slides in a stacked arrangement; and a handle for handling the retaining clip when the plurality of reagent test slides is disposed in a stacked arrangement between the inner surface of the first plate and the inner surface of the third plate.

10. A combination as defined by claim 1, wherein the retaining clip further comprises a handle for handling the retaining clip when the plurality of reagent test slides is disposed in the stacked arrangement between the first cover plate and the second cover plate.

11. A combination as defined by claim 7, wherein the retaining clip further comprises a handle for handling the retaining clip when the plurality of reagent test slides is disposed in the stacked arrangement between the first cover plate and the second cover plate.

12. A retaining clip as defined by claim 9, wherein the handle is unitarily coupled to the outer surface of the second plate.

13. A retaining clip as defined by claim 9, further comprising a third pivotal joining means for pivoting the inner surface of the first plate such that the distance separating the inner surface of the first plate and the inner surface of the third plate is decreased to accommodate a lesser number of reagent test slides in a stacked arrangement.

14. A retaining clip as defined by claim 13, further comprising a fourth pivotal joining means for pivoting the inner surface of the third plate such that the distance separating the inner surface of the first plate and the inner surface of the third plate is decreased to accommodate a lesser number of reagent test slides in a stacked arrangement.

15. A retaining clip as defined by claim 9, which further comprises restraining means coupled to at least the first plate and the third plate for restraining the plurality of test slides in a stacked arrangement.

16. In combination:

a plurality of reagent test slides disposed in a stacked arrangement, each reagent test slide of the plurality of reagent test slides including a frame having opposite lateral edges, and a film portion supported by the frame and being coated with a chemical reagent, each reagent test slide having a width measured between the opposite lateral edges thereof; and a retaining clip as defined by claim 9, wherein the first plate of the retaining clip and the third plate of the retaining clip are dimensioned in width to be less than the widths of the reagent test slides to allow the opposite lateral edges of the reagent test slides to extend beyond the first and third plates of the retaining clip.

17. In combination:

a plurality of reagent test slides disposed in a stacked arrangement, each reagent test slide of the plurality of reagent test slides including a frame, and a film portion supported by the frame and being coated with a chemical reagent; and a retaining clip as defined by claim 9, wherein the stacked arrangement of the plurality of reagent test slides includes an end reagent test slide, and wherein at least one of the first plate and the third plate is dimensioned to entirely cover the film portion of the end reagent test slide of the stacked arrangement.

18. A retaining clip for retaining a plurality of reagent test slides in a stacked arrangement, the retaining clip comprising:

a first plate having an inner surface and an outer surface;

a second plate having an inner surface and an outer surface;

a third plate having an inner surface and an outer surface;

first pivotal joining means for pivoting the inner surface of the first plate towards the inner surface of the second plate;

second pivotal joining means for pivoting the inner surface of the third plate towards the inner surface of the second plate, the first pivotal joining means for pivoting the inner surface of the first plate and the second pivotal joining means for pivoting the inner surface of the third plate allowing the inner surface of the first plate and the inner surface of the third plate to at least partially face each other upon pivoting, the inner surface of the first plate and the inner surface of the third plate being separated by a predetermined distance to define a space therebetween for receiving the plurality of reagent test slides in a stacked arrangement; and restraining means coupled to at least the first plate and the third plate for restraining the plurality of test slides in the stacked arrangement;

wherein the restraining means includes at least one elongated tie member extending from one of the first plate and the third plate, the at least one elongated tie member have a surface and ratchet teeth formed on the surface; at least one slot defining structure situated on one of the first plate and the third plate, the at least one slot defining structure defining a slot for receiving the at least one elongated tie member; and at least one pawl, the at least one pawl extending into the slot of the at least one slot defining structure to engage the ratchet teeth of the at least one elongated tie member.

19. A retaining clip for retaining a plurality of reagent test slides in a stacked arrangement, the retaining clip comprising:

a first plate having an inner surface and an outer surface;

a second plate having an inner surface and an outer surface;

a third plate having an inner surface and an outer surface;

first pivotal joining means for pivoting the inner surface of the first plate towards the inner surface of the second plate;

second pivotal joining means for pivoting the inner surface of the third plate towards the inner surface of the second plate, the first pivotal joining means for pivoting the inner surface of the first plate and the second pivotal joining means for pivoting the inner surface of the third plate allowing the inner surface of the first plate and the inner surface of the third plate to at least partially face each other upon pivoting, the inner surface of the first plate and the inner surface of the third plate being separated by a predetermined distance to define a space therebetween for receiving the plurality of reagent test slides in the stacked arrangement; and restraining means coupled to at least the first plate and the third plate for restraining the plurality of test slides in the stacked arrangement;

wherein the restraining means includes an elastic member, the elastic member encircling the first plate and the third plate to help hold the plurality of reagent test slides in the stacked arrangement therebetween.

20. A retaining clip as defined by claim 19, wherein each of the first plate and the third plate includes a groove formed on the outer surface thereof for at least partially receiving the elastic member.

21. A retaining clip for retaining a plurality of reagent test slides in a stacked arrangement, the retaining clip comprising:
a first plate having an inner surface and an outer surface;
a second plate having an inner surface and an outer surface;
a third plate having an inner surface and an outer surface;
the third plate being rigidly joined at an angle to the second plate, thereby forming a corner between the third plate and the second plate;
first pivotal joining means for pivoting the inner surface of the first plate towards the inner surface of the second plate, the inner surface of the first plate and the inner surface of the third plate being separated by a predetermined distance to define a space therebetween for receiving the plurality of reagent test slides in a stacked arrangement; and
a handle for handling the retaining clip when the plurality of reagent test slides is disposed in a stacked arrangement between the inner surface of the first plate and the inner surface of the third plate.

22. A retaining clip as defined by claim 21, wherein the handle is unitarily coupled to the outer surface of the second plate.

23. A retaining clip as defined by claim 21, which further comprises second pivotal joining means for pivoting the inner surface of the first plate such that the distance separating the inner surface of the first plate and the inner surface of the third plate is decreased to accommodate a lesser number of reagent test slides in a stacked arrangement.

24. A retaining clip as defined by claim 21, which further comprises restraining means coupled to at least the first plate and the third plate for restraining the plurality of test slides in the stacked arrangement.

25. A retaining clip as defined by claim 24, wherein the restraining means includes at least one elongated tie member extending from one of the first plate and the third plate, the at least one elongated tie member have a surface and ratchet teeth formed on the surface; at least one slot defining structure situated on one of the first plate and the third plate, the at least one slot defining structure defining a slot for receiving the at least one elongated tie member; and at least one pawl, the at least one pawl extending into the slot of the at least one slot defining structure to engage the ratchet teeth of the at least one elongated tie member.

26. A retaining clip as defined by claim 24, wherein the restraining means includes an elastic member, the elastic member encircling the first plate and the third plate to help hold the plurality of reagent test slides in the stacked arrangement therebetween.

27. A retaining clip as defined by claim 26, wherein each of the first plate and the third plate includes a groove formed on the outer surface thereof for at least partially receiving the elastic member.

28. In combination:
a plurality of reagent test slides disposed in a stacked arrangement, each reagent test slide of the plurality of reagent test slides including a frame having opposite lateral edges, and a film portion supported by the frame and being coated with a chemical reagent, each reagent test slide having a width measured between the opposite lateral edges thereof; and
a retaining clip as defined by claim 21, wherein the first plate of the retaining clip and the third plate of the retaining clip are dimensioned in width to be less than the widths of the reagent test slides to allow the opposite lateral edges of the reagent test slides to extend beyond the first and third plates.

29. In combination:
a plurality of reagent test slides disposed in a stacked arrangement, each reagent test slide of the plurality of reagent test slides including a frame, and a film portion supported by the frame and being coated with a chemical reagent; and
a retaining clip as defined by claim 21, wherein the stacked arrangement of the plurality of reagent test slides includes an end reagent test slide, and wherein at least one of the first plate and the third plate is dimensioned to entirely cover the film portion of the end reagent test slide of the stacked arrangement.

30. In combination:
a retaining clip for retaining a plurality of reagent test slides in a stacked arrangement, the retaining clip including a first cover plate, a second cover plate and a middle plate, the first cover plate being disposed in at least partial overlying relationship with the second cover plate and thereby defining a space therebetween to receive the plurality of reagent test slides in a stacked arrangement, the first cover plate and the second cover plate being joined to the middle plate; and
a plurality of reagent test slides, each reagent test slide of the plurality of reagent test slides including a frame having opposite lateral edges and a recess formed in each opposite lateral edge, and a film portion supported by the frame and being coated with a chemical reagent, the plurality of reagent test slides being received by the retaining clip and held thereby in a stacked arrangement;
wherein the width of each of the first cover plate and the second cover plate is less than the width of each reagent test slide of the plurality of reagent test slides measured between the recesses formed in the apposite lateral edges such that the first and second cover plates do not overlie the recesses.

31. A combination as defined by claim 30, wherein each reagent test slide of the plurality of reagent test slides has a frame which is trapezoidal in shape.

32. A retaining clip for retaining a plurality of reagent test slides in a stacked arrangement, the retaining clip comprising:
a first plate having an inner surface and an outer surface;
a second plate having an inner surface and an outer surface;
a third plate having an inner surface and an outer surface;

the third plate being rigidly joined at an angle to the second plate, thereby forming a corner between the third plate and the second plate, at least a portion of the first plate being movable towards and away from the third plate, the inner surface of the first plate and the inner surface of the third plate thereby defining an adjustable space therebetween for receiving a variable amount of reagent test slides in a stacked arrangement; and an elastic band disposed around the first and third plates, wherein the elastic band provides a compression force that urges at least a portion of the first plate towards the third plate.

33. A retaining clip as defined by claim 32, wherein at least a portion of the first plate is movable toward and away from the third plate in a parallel relationship.

34. A retaining clip as defined by claim 32, wherein the first plate is pivotally secured to the second plate.

35. A retaining clip as defined by claim 32, which further comprises a handle for handling the retaining clip when the plurality of reagent test slides is disposed in a stacked arrangement between the inner surface of the first plate and the inner surface of the third plate.

36. In combination:

a plurality of reagent test slides disposed in a stacked arrangement; and a retaining clip as defined by claim 32.

* * * * *

UNITED STATES PATENT AND TRADEMARK OFFICE
CERTIFICATE OF CORRECTION

| | | |
|---|---|---|
| PATENT NO. | : 7,588,733 B2 | Page 1 of 1 |
| APPLICATION NO. | : 11/001994 | |
| DATED | : September 15, 2009 | |
| INVENTOR(S) | : Rich et al. | |

It is certified that error appears in the above-identified patent and that said Letters Patent is hereby corrected as shown below:

Amend Item (75) Inventor(s) as follows to add:

--Haydn B. Taylor, Windham, NH (US); James M. Sellers, Elliot, ME (US)--.

Signed and Sealed this

First Day of December, 2009

David J. Kappos
*Director of the United States Patent and Trademark Office*